United States Patent [19]

Colodney et al.

[11] 3,954,961

[45] May 4, 1976

[54] DENTAL POLISHING CREAMS

[75] Inventors: Daniel Colodney, Somerville; Martin Cordon, Highland Park, both of N.J.

[73] Assignee: Colgate-Palmolive Company, New York, N.Y.

[22] Filed: Apr. 30, 1973

[21] Appl. No.: 355,372

Related U.S. Application Data

[63] Continuation-in-part of Ser. No. 301,935, Oct. 30, 1972, abandoned.

[52] U.S. Cl. .................................................. 424/49
[51] Int. Cl.² ............................................ A61K 7/16
[58] Field of Search .............................. 424/49–58

[56] References Cited
UNITED STATES PATENTS 3,060,098   10/1962   Gershon................................ 424/49
3,121,623   2/1964    Nesin..................................... 51/293
3,538,230   11/1970   Pader et al............................ 424/50

FOREIGN PATENTS OR APPLICATIONS 769,865    11/1971   Belgium.............................. 424/49

OTHER PUBLICATIONS

Durham, *American Perfumer and Cosmetics*, Vol. 82, pp. 31 & 32, July 1967.

*Primary Examiner*—Richard L. Huff
*Attorney, Agent, or Firm*—Herbert S. Sylvester; Murray M. Grill; Robert L. Stone

[57] ABSTRACT

A dental cream comprising a dental vehicle a small portion of flat flakes of alpha-alumina and a small proportion of iridescent flakes. The vehicle preferably has dispersed therein amorphous silica or aluminosilicate as a dental abrasive.

5 Claims, 2 Drawing Figures

DENTAL POLISHING CREAMS

This application is a continuation-in-part of Ser. No. 301,935 filed Oct. 30, 1972, now abandoned.

One aspect of this invention relates to a dental cream comprising a dental vehicle, a small proportion of flat flakes of alpha-alumina and a small proportion of iridescent flakes. The invention provides a dental cream which has a unique subdued sparkling and pearlescent appearance and very good enamel polishing properties, and which is also effective for cleaning the teeth, including removal of stain and plaque, with negligible damage to dental hard tissues and enamel. The cream may be formulated in the form of an attractive paste having excellent extrusion characteristics, body, shortness of texture, low tack, and otherwise suitable rheological and mouth feel characteristics and stability, consumer acceptability, effectiveness in promoting hygiene in the dental cavity and a beneficial effect on parts of the dentition which may include the teeth and its adjacent elements or structures including plaque calculus, gingiva, mucous membranes, etc.

The alpha-alumina used in the practice of this invention preferably has a mean (by weight) particle diameter of less than about 7 microns (e.g. about 2 to 7 microns).

Figure 1:

FIG. 1 is a photomicrograph (made with a scanning electron microscope) of the flat alpha-alumina particles.

Figure 2:
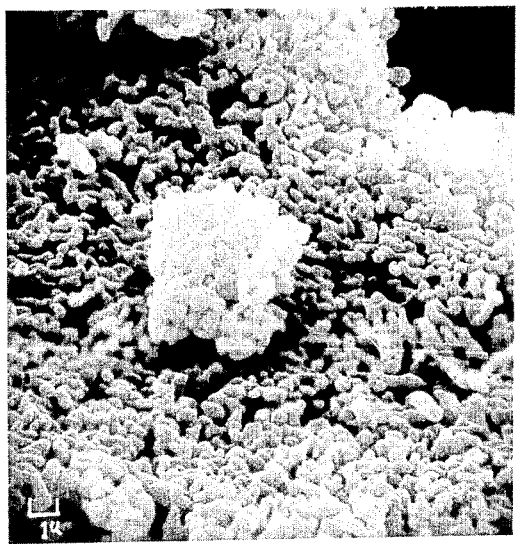

FIG. 2 is a similar photomicrograph of "Linde C" alpha alumina particles. It will be seen that the latter are smoothly rounded shapes, while the flat alumina particles have sharp edges indicating that they have been fractured perpendicular to their flat parallel faces. Generally the thicknesses of the flat flakes are less than about ⅓ (e.g. about 1/5 or 1/10) of their diameters, and are in the range of about ½ micron (or less) to about 2 microns (e.g. about 1 micron).

The flat alpha-alumina crystals, and the process for preparing them, are described in U.S. Pat. No. 3,121,623.

In a preferred form of the invention the iridescent flakes comprise thin transparent mica flakes coated with a thin layer of titanium dioxide. One type of such flakes or platelets has a $TiO_2$ content of about 17%, an average thickness of less than 1 micron (e.g. 0.7 micron), with the longest dimension of most of the platelets being less than about 100 microns, e.g. about 15 to 40 microns, the refractive index of the mica layer being about 1.58 and the refractive index of the $TiO_2$ layer being in the neighborhood of 2.3 to 2.6. The $TiO_2$ coating, in one preferred form, is anatase on both surfaces of the mica flake. The proportion of such flakes employed is dependent on the amount of alpha-alumina present; very good results are obtained when these materials are present in a ratio of about 1:1, such as 1% titanium dioxide-coated mica with 1% alpha-alumina or 0.6% titanium dioxide-coated mica with ½% alpha-alumina. Additional amounts of coated mica may be present, e.g. to give a 2:1 ratio, but this adds to the expense without significantly improving the appearance.

The proportion of alpha-alumina flakes is preferably well below 5% and above 0.1% of the cream, still more preferably less than 2%, e.g. about 1% or about ½%. The proportion of iridescent flakes is also preferably well below 5 and above 0.1%, still more preferably less than 3%, e.g. about 2 or about ½%.

The dental vehicle preferably contains a liquid which is water and/or a humectant such as glycerine, sorbitol, propylene glycol or polyethylene glycol 400, including suitable mixtures thereof. It is usually advantageous to use a mixture of both water and one or two humectants. Polyethylene glycols of higher molecular weight, e.g. polyethylene glycol 600 etc., may also be present. The total liquid content is generally well over 20% by weight of the vehicle (sorbitol, generally present in admixture with water, is considered as a liquid for this purpose). The preferred humectants are glycerine and sorbitol. Typically the vehicle contains about 0-80% by weight of glycerine, about 20 – 80% by weight of sorbitol and about 5 – 80% (preferably less than about 35% and more preferably about 15 – 20%) of water.

The vehicle usually also contains a thickening or gelling agent, such as the natural and synthetic gums and gumlike materials, such as Irish Moss, gum tragacanth, alkali metal (e.g. Li, K or Na) carboxymethyl cellulose and hydroxymethyl carboxyethyl cellulose, polyvinyl pyrrolidone, starch, water soluble hydrophilic colloidal carboxyvinyl polymers such as those sold under the trademark Carbopol 934 and 940, hydroxyethyl cellulose, Indian gum, acacia gums, agar agar, locust bean gum, Laponite CP or SP, which are each synthetic inorganic complex silicate clays sold under trademark by Laporte Industries, Ltd., and pectin or inorganic thickeners such as colloidal silica, e.g. synthetic finely divided silicas including those sold under the trademarks Cab-O-Sil M5, Syloid 244, Syloid 266 and Aerosil D200. The solid portion of the vehicle is typically present in an amount up to about 10% by weight of the toothpaste and preferably within the range of about 0.5–8% by weight.

The dental vehicle is preferably transparent. The art is well acquainted with the formulation of transparent dental vehicles and the adjustments in composition needed to promote transparency. For instance, it is known that the presence of flavoring materials insoluble in the system will decrease transparency and that appropriate changes, e.g. in the surfactant system to increase the solubility of such flavoring materials will increase transparency. It is also within the broader scope of the invention to employ translucent vehicles.

The dental cream preferably also contains a dental abrasive agent which is preferably of the type having an index of refraction so close to that of the vehicle that it does not destroy the transparency of the vehicle when dispersed therein. One suitable material is a porous amorphous silicic anhydride having an average particle size preferably below 20 microns and above 1 micron, a surface area of at least about 200 $m^2/g$, preferably at least about 300 $m^2/g$ and a bulk density of at least about 0.15 $g/cm^3$ and preferably at least about 0.30 $g/cm^3$, such as a dehydrated silica hydrogel (i.e. a xerogel), preferably of the well known regular density or intermediate density type. Examples of such amorphous silicic anhydride dental abrasives are Syloid 63, Syloid 72 and Syloid 74 which are described in "The Davison Family of Syloid Silicas" published by their manufacturer, Grace, Davison Chemical Co. Santocel 100, manufactured by Monsanto, is also a desirable dental abrasive. Syloid 72 has an average particle size of about 4 microns, a surface area of about 340 $m^2/g$ and a bulk density of about 0.177 $g/cm^3$. Syloid 74 has an average particle size of about 8 microns, and a surface area of about 320 $m^2/g$ and a bulk density of about 0.26 $g/cm^3$. For Syloid 63 the corresponding figures are about 9 microns, about 675 m²/g and about 0.4 g/cm³. A grade of Santocel 100 has a surface area of about 239 m²/g and a bulk density of about 0.24 g/cm³. These amorphous silicic anhydrides may be used singly or in mixtures. They are typically employed in amount of about 5–50% preferably about 10–20% of the dental cream. The maximum particle size in the preferred grades of amorphous silicic anhydride polishing agent is desirably below the minimum size of palpability and is typically well below 75 microns. It is within the broad scope of the invention to use other dental abrasive agents particularly those which have a refractive index similar to that of the vehicle.

Another suitable type of dental abrasive agent which may be added to the vehicle in similar amounts is an amorphous alkali metal or alkaline earth metal aluminosilicate preferably having a refractive index of about 1.44–1.47, and containing at least about 70% silica, up to about 10% alumina, up to about 20% by weight of moisture and up to about 10% by weight of sodium oxide. Typically, this material has a particle size of up to about 35 microns, preferably about 1–20 microns, e.g. 2–4 microns. The preferred moisture content is about 10–20% by weight, measured by loss at 1000°C. and the typical content of sodium oxide is about 5–10% by weight. Generally, the agent has a loose bulk density of up to about 0.4g/cc, such as about 0.1 to 0.3g/cc.

The toothpaste may also contain surface active agent, e.g. to achieve increased prophylactic action, assist in achieving thorough and complete dispersion of the instant compositions throughout the oral cavity, and render the instant compositions more cosmetically acceptable. The organic surface active material may be anionic, nonionic, ampholytic, or cationic in nature, and it is preferred to employ as the surface active agent a detersive material which imparts to the composition detersive and foaming properties. Suitable types of such detergents are water soluble salts of higher fatty acid monoglyceride monosulfates, such as sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1,2 hydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl or N-palmitoyl sarcosine, which should be substantially free from soap or similar higher fatty acid material which tends to substantially reduce the effect of those compounds. The use of these sarcosine compounds in dentifrice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface active materials include nonionic agents such as condensates of sorbitan monostearate with approximately 60 moles of ethylene oxide, condensates of ethylene oxide with propylene oxide condensates of propylene glycol ("Pluronics") and amphoteric agents such as quaternized imidazole derivatives, which are available under the trademark "Miranol" such as Miranol C₂M. Cationic surface active germicides and antibacterial compounds such as di-isobutylphenoxyethoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethanoxy groups per molecule) and salts thereof with acids, and compounds of the structure

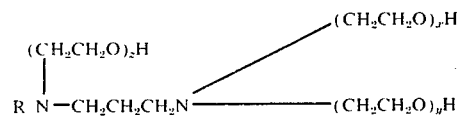

where R is a fatty alkyl group containing from about 12 to 18 carbon atoms, and $x$, $y$ and $z$ total 3 or higher, as well as salts thereof with mineral organic acids, may also be used. It is preferred that the total amount of surface-active agent be about 0.05–5% by weight, preferably about 1–3%, of the dentifrice.

Various other materials may be incorporated in the oral preparation of this invention. Examples thereof are coloring or whitening agents, preservatives, silicones, chlorophyll compounds, ammoniated materials, such as urea, diammoniumphosphate and mixtures thereof, and other constituents. Each of these adjuvants may be typically incorporated in the instant toothpastes in amounts up to about 5%.

The toothpaste may also contain antibacterial agents in amounts of about 0.01–5%. Typical examples of such agents are guanidines, biguanides and amines such as:

$N^1$-(4-chlorobenzyl)-$N^5$-2,4-(dichlorobenzyl) biguanide;
p-chlorophenyl biguanide;
4-chlorobenzhydryl biguanide;
4-chlorobenzhydrylguanylurea;
N-3-lauroxypropyl-$N^5$p-chlorobenzylbiguanide;
1,6-di-p-chlorophenylbiguanidohexane;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine; and
their non-toxic acid addition salts.

Suitable flavoring or sweetening sialagogues may be employed in formulating a flavor for the compositions of the present invention. Examples of suitable flavoring constituents include the flavoring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate and saccharine. Suitably, flavor and sweetening agent may together comprise from about 0.01 to 5% or more of the compositions of the instant invention.

The compositions of the present invention suitably may also contain a fluorine-containing compound having a beneficial effect on the care and hygiene of the oral cavity, e.g. diminution of enamel solubility in acid and protection of the teeth against decay. Examples thereof include sodium fluoride, stannous fluoride, potassium fluoride, potassium stannous fluoride (SnF$_2$.KF), sodium hexafluorostannate, stannous chlorofluoride, sodium fluorozirconate and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

The toothpaste may be prepared by suitably mixing the ingredients. For instance a gelling agent such as sodium carboxymethyl cellulose or Carbopol 934 and a preservative such as sodium benzoate, if employed, is dispersed with a humectant such as glycerine. Water may also be present. Additional humectant and water, as an aqueous 70% sorbitol solution, may then be mixed with the dispersion and a paste, gel or cream is formed. Dental abrasive agent is then added. Surface-active agent, such as sodium lauryl sulfate, if employed, is then dispersed in the mixture together with the alpha-alumina and iridescent flake, after which the desired flavor is added. The toothpaste is then thoroughly de-aerated (e.g. in vacuo) and tubed. Vacuum is also preferably applied during the later mixing stages, as when siliceous dental abrasive, alpha-alumina flakes and iridescent flakes are incorporated.

The following Examples are given to illustrate this invention further. In this application all proportions are by weight unless otherwise indicated.

EXAMPLE 1

A pearlescent toothpaste of excellent tooth polishing characteristics is prepared from the following ingredients: glycerine 25 parts, sorbitol-water mixture (70% sorbitol 30% water) 41.8 parts, sodium aluminosilicate 16 parts, low density silica gel 4 parts, deionized water 3 parts, polyethylene glycol 3 parts, sodium lauryl sulfate 2 parts, chloroform 1 part, alpha-alumina flakes 1 part, titanium dioxide-coated mica flakes 1 part, sodium carboxymethylcellulose 0.35 part, sodium benzoate 0.5 part, sodium saccharin 0.17 part, flavor (essential oil) 1 part, 1% aqueous solution of F D & C yellow No. 5 0.09 part, 1% aqueous solution of F D & C Blue no. 1, 0.09 part. In one case (a) the alpha-alumina flakes have a mean particle diameter of 5 microns, substantially all being less than 12 microns in diameter. In another case (b) the alpha alumina flakes have a mean (by weight) particle diameter of about 4 microns, all the particles thereof have diameters less than 10.1 microns, about 85 – 95% (by weight) have diameters less than 6.0 microns and about 30 – 35% have particle diameters less than 3.5 microns.

The toothpastes show a percent polish recovery of 56 – 59 and a high percent stain removal (e.g. 76). The RDA (measured on Ex. 1b) is 93. In contrast, when 1% of very finely divided zirconium silicate of less than 1 micron average particle size [and of the following particle distribution: 100% below 4 microns, 99% below 2.5 microns, 94% below 2 microns, 72% below 1 micron, 46% below 0.5 micron, 27% below 0.3 micron, 3% below 0.2 micron, (Ultrox 1000W)] is used in place of the alumina flakes the percent polish recovery is 58 and the percent stain removal is about 50, the RDA is 64, and the toothpaste does not have as pronounced a sparkling, pearlescent appearance.

The composition of the sodium aluminosilicate may be expressed empirically as follows: silica about 72%; alumina about 8%; sodium oxide about 7%; water(ignition loss at 1000°C) about 12%. It has a bulk density of about 0.19 – 0.22 g/cm$^3$ a surface area of 120 m$^2$/g, a particle size of about 2 microns (the particles being aggregates of material of ultimate particle size of 35 millimicrons), an oil absorption value of 150 – 160 g/100g and a pH (for a 4% slurry in water) of about 10.5. The titanium dioxide-coated mica flakes (Timica Sparkle) range in size from about 15 – 40 microns; their thickness is about 0.7 microns; their titanium dioxide coatings (on both faces of each flake) are of anatase; and their composition is about 20% anatase, 80% mica. The polyethylene glycol has an average molecular weight of about 600. The low density silica gel has a bulk density of about 0.11 g/cm$^3$, a particle size of about 4 microns, a surface area of 310 m$^2$/g, an oil absorption value of about 310 g/100g and a pH (for a 5% aqueous slurry) of 7.6.

EXAMPLE 2

Example 1 is repeated except that the proportion of alpha-alumina flakes is reduced to 0.5 part and the proportion of titanium dioxide-coated mica flakes to 0.6 part, with corresponding increase in the proportion of sorbitol-water mixture, to 42.7 parts.

EXAMPLE 3

Example 1b is repeated except that the sodium aluminosilicate has the following empirical composition: silica about 78%; alumina about 1%; sodium oxide about 10%, water (determined by loss on ignition at 1000°C) about 10%. It has a surface area of about 225–300 m$^2$/g an oil absorption of about 80–110 g/100 g, a particle size of about 2 to 4 microns and a pH (measured on a 4% slurry in water) of 7.5. The toothpaste shows a percent polish recovery of 57 and a percent stain removal of 84.

EXAMPLE 4

Example 1b is repeated except that the amount of the aluminosilicate is increased to 27% and the amount of the low density silica gel is omitted and the amount of sorbitol-water mixture is decreased to 35 parts.

In each of the above Examples the dental cream in the absence of the alpha-alumina flakes and titanium dioxide-coated mica is a transparent clear colored gel. The inclusion of the alpha-alumina flakes (in the absence of the coated mica) makes this gel translucent(when viewed as an extruded ribbon thereof about 5 mm thick).

The water-soluble dyes may of course be omitted from the foregoing Examples, resulting in a white pearlescent toothpaste of excellent tooth polishing characteristics.

EXAMPLE 5

Dental polishing creams having a less pasty texture are prepared as described in the foregoing Examples by, in each case, reducing proportion of sodium carboxymethylcellulose to 0.2 part, and reducing the amount of low density silica gel to 2 parts and correspondingly increasing the amount of sorbitol-water mixture (e.g. to 44 parts).

While it is most preferred to use alumina flakes whose mean particle diameter is less than five microns (e.g. about 3 to 4 microns) it is within the broader scope of this invention to use alumina flakes of larger diameters but similar thickness, such as alumina flakes, described in the aforesaid U.S. Pat. No. 3,121,623 having average diameters of 9, 12 or 15 or more microns, free of particles over 40 microns in diameter(-preferably free of particles over about 20 microns in diameter) and substantially free of particles having thicknesses above about 3 microns. The bulk density of the finely divided alumina may be measured in the following manner: a 10 ml. graduated cylinder is weighed and filled with the alpha-alumina sample to approximately the 10 ml. mark by pouring the sample through a funnel, the side of the cylinder is then lightly tapped 10 times and the settled volume recorded, the weight of the sample is then measured and the densities recorded. The alumina flakes of Example 1 have bulk densities, so measured, on the order of about 1, e.g. 1.1 to 1.2 g/cm$^3$.

It is also within the broader scope of the invention to use other fine particles of alpha-alumina in place of all or part (e.g. 1/2) of the flakes described above. Thus, one may use the Linde alumina illustrated in FIG. 2 or other similar aluminas having average particle diameters below about 4 microns, e.g. about 1 or 2 microns or less(such as 0.3 micron) or pulverized alpha-aluminas of similar small particle size.

In a preferred form of the invention the alpha-alumina flakes are uncoated and free of adhesion to particles of other materials.

In the stain removal test, sections of human dental enamel are etched with 0.1 N HCl for 2 minutes, rinsed with water, then wet with a dilute solution of stannous fluoride, wiped dry, and finally exposed to a stream of hydrogen sulfide gas which results in the deposition of a brown deposit of stannous sulfide. The amount of stain on the surface is measured with a Gardner Automatic Color Difference meter. The surface is then brushed with a mechanical brushing machine for 3000 reciprocal strokes with a slurry of a dentifrice and the redisual stain measured with the meter. Finally, the stain which remains is completely removed with dental pumice and the reflectance of this surface is read. The ability of a dentifrice to remove the stain is expressed by the following equation.

$$\text{Percent Stain removed} = \text{CUZ}.14/32 \frac{R_d \text{ 3000 strokes} - R_d \text{ initial}}{R_d \text{ pumiced} - R_d \text{ initial}} \, 100$$

where $R_d$ initial, $R_d$ 3000 strokes, and $R_d$ pumiced are respectively the reflectance values measured on the initially stained surface, after brushing for 3000 reciprocal strokes and after removing the residual stain by pumicing.

The percent repolish is determined by a test in which sections of human dental enamel, upon which have been ground flat areas, are first polished, then dulled with chalk, and then brushed with a slurry of a dentifrice for 5000 reciprocal strokes. A "Monsanto Tooth Reflectance Instrument" is employed to measure the specular reflectance of the surface after each step described above. The dulled surface is adjusted so that it is approximately 150 units (Monsanto Instrument) lower than the polished surface. The polishing ability of the dentifrice is expressed by Equation 2.

(Equation 2)

$$\text{Percent Repolish} = \frac{S_R \text{ 5000 strokes} - S_R \text{ dulled}}{S_R \text{ polished} - S_R \text{ dulled}} \, 100$$

Where $S_R$polished, $S_R$dulled and $S_R$5000 strokes are respectively the specular reflectance values of the enamel surface after the initial polishing, after dulling with chalk, and after brushing with a dentifrice slurry.

The RDA values are obtained by a procedure based on a radioactive technique described in the literature; Stookey, C. K. and Muhler, J. C., J. *Dental Research* 47 524 – 538 (1968).

It is also within the broader scope of the invention to use other sizes of titanium dioxide-coated mica (e.g. of 2–20 micron size having a platelet thickness of 0.3 micron, or 5–40 micron size having a platelet thickness of 0.5 micron) or to use other iridescent flakes in place of all or part of the titanium dioxide-coated mica flakes. Thus one may use mother of pearl flakes (a true nacreous secretion found on the inner surfaces of oyster shells and made up of nontoxic $CaCO_3$), which refract light in various wave lengths across the color spectrum. For instance, one may use mother of pearl flakes screened so that they are retained on a 100 mesh (U.S. Standard) sieve (corresponding to a particle size of about 149 microns) and pass through a 30 mesh sieve (corresponding to a particle size of about 590 microns) with the predominant portion being larger than 200 microns.

The mother of pearl flakes can be produced by grinding oyster shells and mechanically separating the mother of pearl flakes from the balance of the ground material, as by flotation. Typically the mother of pearl flakes are flat, smooth-surfaced, less than 50 microns thick (e.g. 10–40 microns), oval-shaped in plane view, and made up of numerous thin parallel layers (e.g. of thickness well below a micron to say 2–3 microns). The mother of pearl flakes may be the sole iridescent flakes in the composition or they may be used in admixture with titanium dioxide-coated mica flakes. Other, less desirable types of iridescent flakes include mica flakes carrying a coating of BiOCl or other substance whose refractive index is different from that of the mica.

In another aspect of the invention the alpha-alumina flakes are replaced in whole or in part (e.g.½) by very fine crystalline silica particles such as those described in British patent specification 1,249,742.

While toothpaste formulations are described in the above Examples, it is also within the broader scope of the invention to prepare more liquid (i.e. pourable) dental creams.

The pH of the dentifrices is generally within the range of about 4 to 10,e.g. about 5 to 8.

Reference is made to the copending application of Cordon filed on the same date, entitled DENTIFRICES, whose entire disclosure is incorporated herein by reference.

The flakes illustrated in FIG. 1 are sold under the name MICROGRIT. In FIG. 1 some (a minor proportion by weight) of the flakes appear to have been so fractured as to be more granular than flake-like.

The particle diameters given in the Examples are determined by conventional methods. Thus the standard liquid sedimentation technique may be used. The calculation of particle diameter from the sedimentation data being made (as is conventional) on the basis of Stokes' Law, disregarding the particular shape of the particles.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A dental cream comprising a dental vehicle having dispersed therein an amount of alpha-alumina flakes within the range of 0.1 to 5% and an amount of iridescent flakes within the range of 0.1 to 5%, said iridescent flakes being selected from the group consisting of mother of pearl and coated mica flakes, the coating on the mica having an index of refraction different from that of mica, said alpha-alumina having an average particle diameter of less than 20 microns and thicknesses of less than about 3 microns.

2. A dental cream as in claim 1 in which the average particle diameter of said alumina flakes is about 2 to 7 microns.

3. A dental cream as in claim 2 in which said iridescent flakes are transparent mica flakes coated on both sides with titanium dioxide, said iridescent flakes having an average thickness of less than 1 micron, and being less than 100 microns in length, said alumina and said iridescent flakes being present in a ratio of about 1:1 and each being present in amount of about ½ to 1%.

4. A dental cream as in claim 2, which is transparent in the absence of its content of alpha-alunina and iridescent flakes and is translucent in the absence of its content of iridescent flakes.

5. A dental cream as in claim 4 containing about 5 to 50% of a dental abrasive which is amorphous silica or amorphous alkali metal or alkaline earth metal silicate having about the same index of refraction as said vehicle.

* * * * *

UNITED STATES PATENT AND TRADEMARK OFFICE
CERTIFICATE OF CORRECTION

PATENT NO. : 3,954,961
DATED : May 4, 1976
INVENTOR(S) : Daniel Colodney and Martin Cordon It is certified that error appears in the above-identified patent and that said Letters Patent are hereby corrected as shown below:

Column 7, lines 43-45, rewrite the equation as follows:

$$\text{Percent Stain removed} = \frac{(Rd_{3000\ strokes} - Rd_{initial}) \cdot 100}{Rd_{pumiced} - Rd_{initial}}$$

Column 7, lines 65-67, rewrite the equation as follows:

$$(\text{Equation 2})\ \text{Percent Repolish} = \frac{(SR_{5000\ strokes} - SR_{dulled}) \cdot 100}{SR_{polished} - SR_{dulled}}$$

Signed and Sealed this

Thirty-first Day of August 1976

[SEAL]

Attest:

RUTH C. MASON
*Attesting Officer*

C. MARSHALL DANN
*Commissioner of Patents and Trademarks*